United States Patent [19]

Differding

[11] Patent Number: 5,478,964
[45] Date of Patent: Dec. 26, 1995

[54] N-FLUOROSULFONIMIDES AND THEIR APPLICATION AS FLUORINATING AGENTS

[75] Inventor: Edmond Differding, Louvain-La Neuve, Belgium

[73] Assignee: Allied-Signal Inc., Morristown, N.J.

[21] Appl. No.: 988,531

[22] Filed: Dec. 10, 1992

Related U.S. Application Data

[62] Division of Ser. No. 843,692, Feb. 28, 1992, Pat. No. 5,254,732.

[51] Int. Cl.$^6$ .............. C07C 311/15; C07C 67/307; C07C 17/02; C07C 231/12
[52] U.S. Cl. .............. 560/103; 556/476; 560/60; 560/82; 560/83; 560/101; 564/218; 568/312; 568/656; 570/127; 570/128; 570/129; 570/147
[58] Field of Search .............. 556/476; 560/60, 560/82, 83, 101, 103; 564/218; 568/312, 656; 570/127, 128, 129, 147

[56] References Cited

U.S. PATENT DOCUMENTS

| | | | |
|---|---|---|---|
| 4,479,901 | 10/1984 | Barnette | 260/239 |
| 4,828,764 | 5/1989 | DesMarteau | 260/397.45 |
| 4,900,867 | 2/1990 | Wilkes et al. | 564/91 |
| 5,003,074 | 3/1991 | Allmendinger et al. | 548/206 |

OTHER PUBLICATIONS

D. Barton et al., *J. Chem. Soc. Perkin I*, 732 (1974).
M. Seguin et al., *J. of Fluorine Chem.*, 15, 201 (1980).
C. Schack et al., *J. of Fluorine Chem.*, 18, 363 (1981).
W. Barnette, *J. Am. Chem. Soc.*, 106, 452 (1984).
J. Foropoulous, Jr. et al., *Inorg. Chem.*, 23, 3720 (1984).
S. Lee et al., *J. Am. Chem. Soc.*, 108, 2445 (1986).
T. Umemoto et al., *Tetrahedron Letters*, 27(28), 3271 (1986).
S. Singh et al., *J. Am. Chem. Soc.*, 109, 7194 (1987).
E. Differding et al., *Tetrahedron Letters*, 29(47), 6087 (1988).
R. Banks et al., *J. of Fluorine Chem.*, 46, 297 (1990).
T. Umemoto et al., *J. Am. Chem. Soc.*, 112, 8563 (1990).
G. Resnati et al., *J. Org. Chem.*, 56, 4925 (1991).
D. DesMarteau et al., *J. of Fluorine Chem.*, 52, 7 (1991).
F. Davis et al., *Tetrahedron Letters*, 32(13), 1631 (1991).
E. Differding et al., *Synlett*, 3, 187 (1991).
E. Differding et al., *Synlett*, 395 (1991).
E. Differding et al., *Tetrahedron Letters*, 32(31), 3815 (1991).

*Primary Examiner*—Peter O'Sullivan
*Attorney, Agent, or Firm*—Darryl L. Webster; Melanie L. Brown; Jay P. Friedenson

[57] ABSTRACT

The invention describes N-fluorosulfonimides which are useful as fluorinating agents. The N-fluorosulfonimides are stable, easily synthesized, and allow the introduction of fluorine into organic compounds under mild conditions.

13 Claims, No Drawings

N-FLUOROSULFONIMIDES AND THEIR APPLICATION AS FLUORINATING AGENTS

This application is a division of the application Ser. No. 843,692, filed Feb. 28, 1992, now U.S. Pat. No. 5,254,732.

BACKGROUND OF THE INVENTION

This invention relates to N-fluorosulfonimides and their use in the fluorination of nucleophilic organic compounds such as enolethers, aromatics, and organometallic species.

Fluorine substituents are playing an increasingly important role in the search for pharmaceutical and agrochemical agents because the physicochemical properties and the biological activity of target molecules may be modified. See for example BIOMEDICINAL ASPECTS OF FLUORINE CHEMISTRY, Elsevier Biomedical Press, 1982.

Electrophilic fluorination agents allow the introduction of fluorine into target molecules under mild conditions. Fluorination agents containing a nitrogen-fluorine bond are known. U.S. Pat. No. 5,003,074 and E. Differding et al., "New Fluorinating Reagents—The First Enantioselective Fluorination Reaction", Tetrahedron Letters 29(47), 6087 (1988) teach the use of N-fluorosultams in the selective fluorination of carbanions. N-fluorosultams are disadvantageous because they are insufficiently reactive to fluorinate less reactive nucleophiles such as enol ethers and aromatics.

More reactive N-F reagents are known to react with such nucleophiles, but they suffer from other deficiencies. C. Schack et al., "Substitution and Addition Reactions of $NF_4BF_4$ with Aromatic Compounds", J. Fluorine Chem. 18, 363 (1981) teach that $NF_4BF_4$ is a useful fluorination agent but access to the $NF_4BF_4$ is difficult.

T. Umemoto et al., "N-Fluoropyridinium Triflate and its Analogs, The First Stable 1:1 Salts of Pyridine Nucleus and Halogen Atom", Tetrahedron Letters 27(28), 3271 (1986) and T. Umemoto et al., "Power and Structure-Variable Fluorinating Agents—The N-Fluoropyridinium Salt System", J. Am. Chem. Soc. 112, 8563 (1990) teach that N-fluoropyridinium salts are useful fluorinating agents but unfortunately they undergo side-reactions with carbanionic nucleophiles.

R. Banks et al., "N-Halogeno Compounds—Part II—Perfluoro-[N-fluoro-N-(4-pyridyl)-methanesulphonamide —A Powerful New Electrophilic Fluorinating Agent", J. Fluorine Chem. 46, 297 (1990) teaches that perfluoro-[N-fluoro-N-(4-pyridyl )methanesulphonamide] is a useful fluorinating agent. Unfortunately, the preparation of perfluoro-[N-fluoro-N-(4-pyridyl)methanesulphonamide] involves at least six steps and perfluoro-N-(4-pyridyl)methanesulphonamide] cannot be used with aromatic solvents such as benzene or toluene because it reacts with these solvents.

N-fluorosulfonamides are known to be useful as fluorinating agents. For example, U.S. Pat. No. 4,479,901; M. Seguin et al., "Action de $CF_3$ of Sur Des Aziridines N-Substituees", J. Fluorine Chem. 15, 201 (1980); W. Barnette, "N-Fluoro-N-alkylsulfonamides: Useful Reagents for the Fluorination of Carbanions", J. Am. Chem. Soc. 106, 452 (1984); and U.S. Pat. No. 4,900,867 teach that N-fluoro-N-alkylsulfonamides such as N-fluoro-N-neopentyl-p-toluenesulfonamide are useful in the fluorination at a carbon atom of a carbanion. S. Lee et al., "Stereospecific Synthesis of Alkenyl Fluorides. (with Retention) via Organometallic Intermediates", J. Am. Chem. Soc. 108, 2445 (1986) teach that N-fluoro-N-alkylsulfonamides such as N-tert-butyl-N-fluorobenzenesulfonamide are useful in the fluorination of alkenyl iodides. N-fluoro-N-alkylsulfonamides are disadvantageous to use because in preparation, N-fluoro-N-alkylsulfonamides are difficult to isolate and thus, require either column chromatography or low pressure distillation and organometallics or strongly basic anions cause β-elimination of HF from the reagent.

U.S. Pat. No. 4,828,764; J. Foropoulos, Jr. et al., "Synthesis, Properties, and Reactions of Bis((trifluoromethyl)sulfonyl)imide, $(CF_3SO_2)_2NH$", Inorg. Chem. 23, 3720 (1984).; S. Singh et al., "N-Fluoroperfluoroalkylsulfonimides: Remarkable New Fluorination Reagents", J. Am. Chem. Soc. 109, 7194 (1987); G. Resnati et al., "N-Fluorobis[ (trifluoromethyl)sulfonyl]imide: An Efficient Reagent for the α-Fluorination of Functionalized Carbonyl Compounds", J. Org. Chem. 56, 4925 (1991); and D. Desmarteau et al., "N-Fluoro-N-Bis(trifluoromethanesulfonyl )imide—An Improved Synthesis", J. Fluorine Chem. 52, 7 (1991) teach that N-fluoroperfluoroalkylsulfonimides such as N-fluorobis(trifluoromethanesulfonyl)imide are useful in the fluorination of organic compounds. Unfortunately, N-fluoroperfluoroalkylsulfonimides are disadvantageous to use because a five step synthesis for their preparation is required, they are hydroscopic, they cannot be used with aromatic solvents such as benzene or toluene because they react with these solvents, and they require special handling because they react glass.

F. Davis et al., "N-Fluoro-o-benzenedisulfonimide: A Useful New Fluorinating Reagent", Tetrahedron Letters 32(13), 1631 (1991) teach that N-fluoro-o-benzenesulfonimide is useful in the fluorination of enolates and carbanions. N-fluoro-o-benzenedisulfonimide is disadvantageous to use because the preparation of the starting material, o-benzenedisulfonimide, is difficult and N-fluoro-o-benzenedisulfonimide is unable to fluorinate toluene even upon heating.

N-fluoro-p-fluoro-benzenesulfonimide is known from D. Barton et al., J. Chem. Soc. Perkin Trans. 1, 732 (1974) but the reference does not teach any use for N-fluoro-p-fluoro-benzenesulfonimide.

Thus, the need exists in the art for a new electrophilic fluorinating agent which is easy to make and fluorinates less reactive nucleophiles.

SUMMARY OF THE INVENTION

Surprisingly it has now been found that N-fluorosulfonimides of the Formula I below behave as electrophilic fluorinating agents which combine safe handling and easy access with the capacity to fluorinate nucleophiles ranging from aromatics to carbanions.

Thus, the present invention provides N-fluorosulfonimides of the Formula I $$R_1SO_2\text{—}NX\text{—}O_2SR_2 \qquad (I)$$

wherein X represents an isotope or natural isotopic mixture of fluorine, and $R_1$ and $R_2$ independently are phenyl or naphthyl, which is unsubstituted or substituted by at least one substituent selected from the group consisting of alkyl groups having 1 to 6 carbon atoms, alkoxy groups having 1 to 6 carbon atoms, alkylsulfonyl groups having 1 to 6 carbon atoms, perfluoroalkylsulfonyl groups having 1 to 6 carbon atoms, mono- to per-fluoroalkyl groups having 1 to 6 carbon atoms, cyano, chlorine, and bromine.

Other advantages of the present invention will become apparent from the following description.

DETAILED DESCRIPTION OF THE INVENTION

Preferred substituents on the phenyl or naphthyl include alkyl groups having 1 to 4 carbon atoms, alkoxy groups having 1 to 4 carbon atoms, alkylsulfonyl groups having 1 to 4 carbon atoms, perfluoroalkylsulfonyl groups having 1 to 4 carbon atoms, and mono- to per-fluoroalkyl groups having 1 to 4 carbon atoms. Examples of alkyl groups are methyl, ethyl, n-propyl and i-propyl while preferred examples are methyl and ethyl. Examples of alkoxy groups are methoxy and ethoxy. Examples of alkylsulfonyl groups are methylsulfonyl and ethylsulfonyl. Examples of perfluoroalkylsulfonyl groups are trifluoromethylsulfonyl and pentamethylsulfonyl. Examples of fluoroalkyl groups are fluoroethyl; 1,1-difluoroethyl; 1,2-difluoroethyl; 1,1,1,-trifluoroethyl; 1,1,2,2,-tetrafluoroethyl; perfluoroethyl; and trifluoromethyl.

A preferred embodiment of the invention is when $R_1$ and $R_2$ are the same in Formula (I) above. More preferably, $R_1$ and $R_2$ are unsubstituted or substituted phenyl. Preferably, $R_1$ and $R_2$ have one or two substituents.

A more preferred group of compounds of Formula I above is where $R_1$ and $R_2$ are phenyl or naphthyl which is unsubstituted or substituted by at least one substituent selected from the group consisting of alkyl groups having 1 to 6 carbon atoms, perfluoroalkyl groups having 1 to 6 carbon atoms, cyano, chlorine, and bromine.

An even more preferred group of compounds of Formula I above is where $R_1$ and $R_2$ are phenyl which is unsubstituted or substituted by at least one substituent selected from the group consisting of alkyl groups having 1 to 6 carbon atoms, perfluoroalkyl groups having 1 to 6 carbon atoms, cyano, chlorine, and bromine.

Examples of compounds of Formula I above are N-fluoro-p-methoxybenzenesulfonimide, N-fluoro-p-ethoxy-benzenesulfonimide, N-fluoro-p-methyl-benzenesulfonimide, N-fluoro-p-ethyl-benzenesulfonimide, N-fluoro-p-methylsulfonyl-benzenesulfonimide, N-fluoro-p-perfluoroethylsulfonyl-benzenesulfonimide, N-fluoro-p-trifluoromethylbenzenesulfonimide, N-fluoro-p-cyano-benzenesulfonimide, N-fluoro-p-chloro-benzenesulfonimide, and N-fluoro-p-bromo-benzenesulfonimide.

The most preferred embodiment is when $R_1$ and $R_2$ are both phenyl; Formula I then represents N-fluorobenzenesulfonimide.

The compounds of Formula I which contain fluorine isotopes may be used to synthesize labelled target molecules.

The N-fluorobenzenesulfonimides may be obtained by the procedure described by K. Auer et al, Chimia 44, 120 (1990). The benzenesulfonimides of the formula $R_1SO_2$—NH—$O_2SR_2$ which are known (obtainable by known processes or in some cases commercially available) are reacted with one equivalent of fluorine in admixture with an inert gas in acetonitrile at −40° C. in the presence of powdered sodium fluoride in an ambient pressure reactor. The inert gas may be argon, helium, or nitrogen, preferably nitrogen on cost grounds. An excess of fluorine must be avoided since it may lead to the fluorination of the aromatic rings. It is advantageous to use mixture of 1 to 20 vol.-% fluorine in the inert gas.

The present invention also provides a process for the electrophilic fluorination of organic compounds which comprises the step of: reacting one equivalent of the nucleophilic organic compound with at least one equivalent of a compound of Formula I above.

Preferred nucleophilic organic compounds include unsubstituted or substituted aromatic or heteroaromatic compounds, enol ethers, carboxylic acid esters, ketones and metallized organic compounds, which may be aliphatic, aromatic, or olefinic. Preferred substituted aromatic compounds include toluene ($C_6H_5CH_3$), trans 1-phenyl-2-iodopropene (trans-$C_6H_5CHCICH_3$), and acetanilide ($C_6H_5NHCOCH_3$). A preferred enol ether is trimethyl-silyloxycyclohexene (($CH_3)_3SiOC_6H_9$).

Preferred carboxylic acid esters include methyl 2,2-diphenylethanoate (($C_6H_5)_2CHCOOCH_3$), diethyl phenylmalonate ($C_6H_5CH(COOCH_2CH_3)_2$), and ethyl phenylacetate ($C_6H_5CH_2CO_2C_2H_5$). Preferred ketones include anisole ($C_6H_5OCH_3$), propiophenone ($C_6H_5COCH_2CH_3$), and 2-methyl-1-tetralone ($C_6H_4(CH)_2(CH_2)_2COCHCH_3$). Preferred metallized organic compounds include anthracenyl lithium (prepared by reacting 9-bromoanthracene with n-butyl lithium) and 1-phenyl-2-lithio-propene (prepared by reacting 1-phenyl-2-iodo-propene with tert-butyl lithium). Toluene, 9-bromoanthracene, acetanilide, diethyl phenylmalonate, ethyl phenylacetate, anisole, propiophenone, and 2-methyl-1-tetralone are commercially available.

Fluorination may be effected after first metallizing the nucleophile. Metallization may occur, for example, with an alkali metal such as lithium, sodium or potassium. Enolates, for example, may be fluorinated by first treating the carbonyl compound with a base such as lithium diisopropylamide or potassium hexamethyldisilazide in tetrahydrofuran between about −100° C. and about −70° C., warming to room temperature in the presence of the fluorinating agent, and quenching with 0.1N hydrogen chloride.

The proportions of nucleophile to fluorinating agent may be between about 50:1 molar equivalents nucleophile to fluorinating agent so that the nucleophile is present in excess as solvent and about 1:3 so that the fluorinating agent is present in excess.

The reactivity of the nucleophile is generally temperature-dependent. The reaction may be conducted in the temperature range of about −115° C. to about +150° C. and preferably about −80° C. to about 100° C., depending on the nature of the precursor to be fluorinated.

The reaction may be carried out in the presence of an inert solvent or without solvent. It is advantageous to use an excess of the nucleophilic organic compound when no solvent is used.

Suitable inert solvents are non-polar or polar and preferably are aprotic. At least one solvent is used and mixtures of at least two different solvents may be used. Examples of preferred solvents are ethers, halogenated hydrocarbons, carboxylic acid esters and lactones, N-substituted carboxylic acid amides and N-substituted lactams, sulfoxides, sulfones, tertiary amines, hydrocarbons, and nitriles.

Preferred ether solvents include dibutylether, tetrahydrofuran, dioxane, ethylene glycol-monomethyl or -dimethyl ether, ethylene glycol-monoethyl or -diethyl ether, diethylene glycol diethyl ether, and triethylene glycol dimethyl ether. Preferred halogenated hydrocarbon solvents include dichloromethane, chloroform, 1,2-dichloroethane, 1,1,1-trichloroethane, and 1,1,2,2-tetrachloroethane. Preferred carboxylic acid esters and lactone solvents include ethylethanoate, propylmethanoate, benzoylmethanoate, 2-methoxyethylacetate, γ-butyrolactone, δ-valerolactone, and pivalolactone. Preferred N-substituted carboxylic acid amides and N-substituted lactams include N,N-dimethylformamide; N,N-diethylformamide; N,N-dimethylacetamide; tetramethylurea; hexamethylphosphoric triamide; N-methylpyrrolidone; and N-acetylpyrrolidone). A preferred sulfoxide solvent is dimethylsulfoxide. Preferred sulfone solvents include dimethylsulfone, diethylsulfone, trimethylsulfone, and tetramethylsulfone. Preferred tertiary amine solvents include N-methylpiperidine and N-methylmorpholin. Preferred hydrocarbon solvents include pentane, hexane, cyclohexane, and nonane. Preferred nitrile solvents include acetonitrile and propionitrile.

Where fluorination occurs on the benzene ring, a mixture of ortho- and para-fluorinated product, and possibly meta-isomer forms. The regioselectivity is to some extent temperature-dependent.

It has also been found that the most nucleophilic C—H bond in carboxylic acid esters and ketones is fluorinated preferably, for example

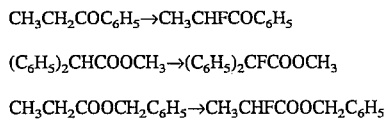

The fluorination process may be carried out as follows. The fluorinating agent is mixed with the nucleophile and optionally a solvent and then reacted at a temperature between about −115° C. and about +200° C. for between about 0.5 hour and about 300 hours. The mixture is quenched if necessary, e.g. with ammonium chloride solution, and neutralized, e.g. with hydrogen chloride solution. The organic layer is extracted, e.g. with diethyl ether or dichloromethane, washed, and the fluorinated product is purified by distillation, crystallization, or chromatography.

When the nucleophilic organic compound is used as the solvent and is low-boiling, the reaction mixture may be refluxed for between about 1 and about 300 hours.

The advantages of the present invention are as follows: facile synthesis and easier access of the compounds of Formula I above, fluorination under mild conditions, easier handling and therefore more practical reagents, sufficiently reactive to fluorinate less reactive nucleophiles such as enol ethers and aromatics, and fewer side-reactions with carbanionic nucleophiles.

The present invention is more fully illustrated by the following non-limiting Examples.

For the following Examples, the apparatus was flushed through with argon prior to reaction. Cooling was effected using liquefied nitrogen or air and hexane, or dry ice in isopropanol.

EXAMPLE I

This Example is directed to the synthesis of N-fluorobenzenesulfonimide.

80 millimoles di-benzenesulfonimide were dissolved in 500 milliliters acetonitrile and 640 millimoles sodium fluoride were added. The mixture was cooled to −35° C. and a 10 vol.% $F_2/N_2$ gas mixture was bubbled through for 2 hours. The reaction mixture was flushed through with $N_2$ for an additional 2 hours. After filtration and evaporation, N-fluorobenzenesulfonimide was obtained as white crystals in 74% yield.

The remaining Examples are directed to the fluorination of organic compounds with the N-fluorobenzenesulfonimide prepared according to Example 1 above.

EXAMPLE 2

This Example is directed to the fluorination of anisole ($C_6H_5OCH_3$) to form ortho-fluoroanisole and para-fluoroanisole ($C_6H_4FOCH_3$).

632 milligrams of N-fluorobenzenesulfonimide prepared according to Example 1 above were dissolved in 5 milliliters (4.97 grams) anisole (22 molar equivalents) and stirred at 150° C. for 5 hours. The mixture was purified on a silica gel column. 57% ortho- and 37% para-fluorination was identified using $^{19}$F-NMR (fluorobenzene as internal standard). 100% yield was obtained.

EXAMPLE 3

The procedure of Example 2 was repeated except that stirring continued for 24 hours at 100° C. 19% ortho- and 14% para-fluorination was found and a 33% yield was obtained.

EXAMPLE 4

This Example is directed to the fluorination of toluene ($C_6H_5CH_3$) to form ortho-fluorotoluene, meta-fluorotoluene, and para-fluorotoluene ($C_6H_4FCH_3$).

1 equivalent N-fluorobenzenesulfonimide (3.15 milligrams) prepared according to Example 1 above was dissolved in 5 milliliters (50 equivalents) toluene and refluxed for 9 days. A 19% yield was obtained with the proportions ortho:meta:para in the ratio of 65:7:28.

EXAMPLE 5

This Example is directed to the fluorination of trimethylsilyloxycyclohexene $((CH_3)_3SiOC_6H_9)$ to form 2-fluorocyclohexanone ($C_6H_9OF$).

A solution of 5 millimoles trimethyl-silyloxycyclohexene in 10 milliliters dichloromethane was dropped into a solution of 6 millimoles N-fluorobenzenesulfonimide prepared according to Example 1 above in 15 milliliters dichloromethane. The mixture was stirred for 24 hours at room temperature. 60 milliliters 0.1N hydrogen chloride were poured into the mixture and stirring was continued for 10 minutes. The mixture was extracted with dichloromethane and the organic layers were washed with water and brine. A 47% yield of 2-fluorocyclohexanone was obtained.

EXAMPLE 6

This Example is directed to the fluorination of propiophenone ($C_6H_5COCH_2CH_3$) to form 2-fluoropropiophenone ($C_6H_5COCHFCH_3$).

1 millimole propiophenone in tetrahydrofuran was dropped into a stirred solution of lithium diisopropylamine in 2 milliliters tetrahydrofuran at −78° C. After 1 hour of stirring, a solution of 1.2 millimoles N-fluorobenzenesulfonimide prepared according to Example 1 above in 3 milliliters tetrahydrofuran was dropped into the reaction mixture and stirring was continued at −78° C. The temperature of the reaction mixture was allowed to rise to 25° C., stirring was continued for 1 hour, and the reaction was quenched by pouring the mixture into saturated ammonium chloride solution. The mixture was neutralized with 1N hydrogen chloride solution and extracted with dichloromethane and the organic phase was washed with water.

2-fluoropropiophenone was obtained in 85% yield.

EXAMPLE 7

This Example is directed to the fluorination of anthracenyl lithium ($C_6H_4(CH)(CLi)(C_6H_4)$ to form 9-fluoroanthracene ($C_6H_4(CH)(CF)C_6H_4$).

1.2 millimoles n-butyl lithium were dropped into a solution of 1 millimole bromoanthracene in 5 milliliters diethyl ether at 5° C. The solution was cooled to 0° C., was stirred for 1 hour, and then was cooled further to −78° C.; 1.2 millimoles N-fluorobenzenesulfonimide prepared according to Example 1 above in 5 milliliters tetrahydrofuran were dropped into the mixture which was stirred for 1 hour. The temperature was allowed to rise to 20° C. while stirring was continued. The reaction mixture was quenched by pouring into saturated ammonium chloride solution and extracted with diethyl ether. Fluoroanthracene was obtained in 76% yield.

EXAMPLE 8

This Example is directed to the fluorination of trans 1-phenyl-2-iodopropene (trans-$C_6H_5CHCICH_3$) to form trans 1-phenyl-2-fluoropropene (trans-$C_6H_5CHCFCH_3$).

A 4:1:1 mixture of tetrahydrofuran, pentane and diethyl ether respectively was prepared. 488 milligrams (2 moles) trans-$C_6H_5CHCICH_3$ in 17 milliliters of the solvent mixture were stirred with t-butyllithium in 3.1 milliliters pentane at −110° C. for 1 hour. 945 milligrams (3 moles) N-fluorobenzenesulfonimide prepared according to Example 1 above in 5 milliliters of the solvent mixture were dropped into the mixture which was stirred and allowed to warm up to room temperature. The reaction mixture was poured into an ice/water bath with 0.1N hydrogen chloride, extracted with dichloromethane, dried with magnesium sulfate, and evaporated. A 17% yield of trans 1-phenyl-2-fluoropropene was obtained.

EXAMPLE 9

This Example is directed to the fluorination of acetanilide ($C_6H_5NHCOCH_3$) to form fluoroacetanilide ($C_6H_4FNHCOCH_3$)

A mixture of 5 millimoles N-fluorobenzenesulfonimide prepared according to Example 1 above with 10 millimoles acetanilide was stirred for 18 hours at 100° C. The mixture was purified on a silica gel column. A 40% yield of $C_6H_4FNHCOCH_3$ in an ortho:meta:para ratio of 62:0:38 was achieved.

EXAMPLE 10

This Example is directed to the fluorination of (($C_6H_5)_2CHCOOCH_3$) to form ($C_6H_5)_2CFCOOCH_3$.

4.8 milliliters $KN(SiCH_3)_2$ were dropped into 5 milliliters ($C_6H_5)_2CHCOOCH_3$ in tetrahydrofuran at −78° C. and the resulting yellow suspension was stirred for 45 minutes. 1.2 molar equivalents N-fluorobenzenesulfonimide prepared according to Example 1 above in 4 milliliters tetrahydrofuran were dropped into the mixture and stirring continued at −78° C. for 1 hour. The mixture was allowed to warm up to room temperature, quenched with ammonium chloride, and acidified with 0.1N hydrogen chloride. Extraction with dichloromethane, drying, and evaporation were followed by purification on a silica gel column. White crystalline ($C_6H_5)_2CFCOOCH_3$ was obtained in 82% yield.

EXAMPLE 11

This Example is directed to the fluorination of diethyl phenylmalonate ($C_6H_5CH(COOCH_2CH_3)_2$) to form $C_2H_5CF(COOCH_2CH_3)_2$.

1 millimole of diethyl phenylmalonate was stirred with potassium hydride in 2 milliliters ether for 30 minutes at −25° C. 1.2 molar equivalents N-fluorobenzenesulfonimide prepared according to Example 1 above in 2 milliliters ether were dropped into the mixture which was stirred for 1 hour at −20° C. The mixture was allowed to warm up to room temperature and water was added. The product was extracted into ether which was dried and evaporated. Purification was carried out on a silica gel column. $C_6H_5CF(COOCH_2CH_3)_2$ was obtained in 47% yield.

EXAMPLE 12

This Example is directed to the fluorination of 2-methyl-1-tetralone ($C_6H_4(CH_2)_2COCHCH_3$) to form 2-methyl-2-fluorotetralone ($C_6H_4(CH_2)_2COCFCH_3$).

0.16 milliliter diisopropylamine in 10 milliliters tetrahydrofuran were allowed to stand with 1.15 equivalents butyllithium at −25° C. The resulting solution of lithium diisopropylamine was cooled to −78° C. and 1 equivalent 2-methyl-1-tetralone in 5 milliliters tetrahydrofuran solution was dropped in. The mixture was allowed to stand at −70° C. for 100 minutes. 1.5 equivalents N-fluorobenzenesulfonimide prepared according to Example 1 above in 11 milliliters tetrahydrofuran were mixed rapidly with the mixture at −95° C. The mixture was quenched with 30 milliliters ammonium chloride solution and extracted with dichloromethane. The organic phase was dried with magnesium sulfate, filtered, and evaporated. 2-methyl-2-fluoro-tetralone was obtained in 50% yield.

EXAMPLE 13

This Example is directed to the fluorination of ethyl phenylacetate ($C_6H_5CH_2CO_2C_2H_5$) to form $C_6H_5CH_2CO_2CHFCH_3$.

The precursor was stirred with 2 millimoles lithium diisopropylamine (preparation described in Example 12) in tetrahydrofuran at −78° C. for 1 hour. 1.2 equivalents N-fluorobenzenesulfonimide prepared according to Example 1 above in 3 milliliters tetrahydrofuran were added to the mixture which was stirred for 80 minutes. Stirring was continued as the mixture was allowed to warm up to room temperature, quenched with ammonium chloride, extracted with dichloromethane, dried, and evaporated. Purification was carried out on a silica gel column. $C_6H_5CH_2OCOCHFCH_3$ was obtained in 47% yield.

E. Differding et al., "N-Fluorobenzenesulfonimide—A Practical Reagent for Electrophilic Fluorinations", Synlett 3, 187 (March 1991) is incorporated herein by reference. E. Differding et al., "Electrophilic Fluorinations with N-Fluorobenzenesulfonimide: Convenient Access to α-Fluoro- and α,α-Difluorophosphonates", Synlett, 395 (June 1991) teach that N-fluorobenzenesulfonimide is the reagent of choice for the electrophilic fluorination of alkyl phosphonate anions. E. Differding et al., "Nucleophilic Substitution Versus Electron Transfer: On the Mechanism of Electrophilic Fluorinations", Tetrahedron Letters 32(31), 3815 (1991) teach that N-fluorobenzenesulfonimide is useful in the fluorination of citronellic ester enolate.

Having described the invention in detail and by reference to preferred embodiments thereof, it will be apparent that modifications and variations are possible without departing from the scope of the invention defined in the appended claims.

What is claimed is:

1. A process for the electrophilic fluorination of organic compounds which comprises the step of: reacting one equivalent of a nucleophilic organic compound with at least one equivalent of a compound of the formula $$R_1SO_2-NX-O_2SR_2$$

wherein X represents an isotope or natural isotopic mixture of fluorine, and $R_1$ and $R_2$ independently are phenyl or naphthyl, which is unsubstituted or substituted by at least one substituent selected from the group consisting of alkyl groups having 1 to 6 carbon atoms, alkoxy groups having 1 to 6 carbon atoms, alkylsulfonyl groups having 1 to 6 carbon atoms, perfluoroalkylsulfonyl groups having 1 to 6 carbon atoms, mono- to per-fluoroalkyl groups having 1 to 6 carbon atoms, cyano, chlorine, and bromine.

2. The process of claim 1 wherein said nucleophilic organic compound is selected from the group consisting of unsubstituted or substituted aromatic or heteroaromatic compounds, enol ethers, carboxylic acid esters, ketones and-metallized organic compounds, which may be aliphatic, aromatic or-olefinic.

3. The process of claim 1 wherein said nucleophilic organic compound is substituted aromatic compound.

4. The process of claim 1 wherein said nucleophilic organic compound is enol ether.

5. The process of claim 1 wherein said nucleophilic organic compound is carboxylic acid ester.

6. The process of claim 1 wherein said nucleophilic organic compound is ketone.

7. The process of claim 1 wherein said nucleophilic organic compound is metallized organic compound.

8. The process of claim 1 wherein the reaction temperature is between about $-115°$ C. and about $+150°$ C., 9. The process of claim 1 wherein the reaction mixture is refluxed for between about 0.5 to about 300 hours.

10. The process of claim 1 wherein said reaction occurs in an inert solvent.

11. The process of claim 10 wherein said solvent is selected from the group consisting of ethers, halogenated hydrocarbons, carboxylic acid esters, lactones, N-substituted carboxylic acid amides, N-substituted lactams, sulfoxides, sulfones, tertiary amines, hydrocarbons, and nitriles.

12. The process of claim 10 wherein the solvent is selected from the group consisting of tetrahydrofuran, dichloromethane, pentane, diethyl ether, hexane, and isopropanol.

13. The process of claim 10 wherein said reaction occurs in a solvent comprising at least two different solvents.

* * * * *